(12) United States Patent
Whitehurst et al.

(10) Patent No.: US 8,452,407 B2
(45) Date of Patent: May 28, 2013

(54) METHODS FOR TREATING GASTROINTESTINAL DISORDERS

(75) Inventors: Todd K Whitehurst, Santa Clarita, CA (US); James P McGivern, Stevenson Ranch, CA (US); Rafael Carbunaru, Studio City, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1136 days.

(21) Appl. No.: 11/192,750

(22) Filed: Jul. 29, 2005

(65) Prior Publication Data

US 2006/0036293 A1 Feb. 16, 2006

Related U.S. Application Data

(60) Provisional application No. 60/601,801, filed on Aug. 16, 2004.

(51) Int. Cl.
*A61N 1/00* (2006.01)
*A61N 1/375* (2006.01)
*A61N 1/36* (2006.01)

(52) U.S. Cl.
CPC ............ *A61N 1/375* (2013.01); *A61N 1/36007* (2013.01)
USPC .............................................. 607/40; 607/36

(58) Field of Classification Search
USPC ..................................................... 607/36, 40
See application file for complete search history.

(56) References Cited

U.S. PATENT DOCUMENTS

| | | | |
|---|---|---|---|
| 3,760,984 A | 9/1973 | Theeuwes | |
| 3,845,770 A | 11/1974 | Theeuwes et al. | |
| 3,916,899 A | 11/1975 | Theeuwes et al. | |
| 3,923,426 A | 12/1975 | Theeuwes | |
| 3,987,790 A | 10/1976 | Eckenhoff et al. | |
| 3,995,631 A | 12/1976 | Higuchi et al. | |
| 4,016,880 A | 4/1977 | Theeuwes et al. | |
| 4,036,228 A | 7/1977 | Theeuwes | |
| 4,111,202 A | 9/1978 | Theeuwes | |
| 4,111,203 A | 9/1978 | Theeuwes | |
| 4,203,440 A | 5/1980 | Theeuwes | |
| 4,203,442 A | 5/1980 | Michaels | |
| 4,210,139 A | 7/1980 | Higuchi | |

(Continued)

FOREIGN PATENT DOCUMENTS

WO WO-97/31679 A2 9/1997
WO WO-97/31679 A3 9/1997

(Continued)

OTHER PUBLICATIONS

Bardhan, K.D., "Is there any Acid Peptic Disease that is Refractory to Proton Pump Inhibitors?", Ailment Pharmacol Ther, vol. 7, (1), (1993), pp. 13 31.

(Continued)

*Primary Examiner* — Nicole F Lavert
(74) *Attorney, Agent, or Firm* — Vista IP Law Group LLP

(57) ABSTRACT

A small implantable stimulator(s) having at least two electrodes is implanted adjacent to a gastrointestinal nerve and/or muscle for the stimulation treatment of gastrointestinal disorders, including gastrointestinal motility, sphincteric disorders, and/or eating disorders. The stimulator provides a means of stimulating tissue at a stimulation site when desired, and may be implanted via a minimal surgical procedure.

21 Claims, 9 Drawing Sheets

U.S. PATENT DOCUMENTS

| | | | |
|---|---|---|---|
| 4,327,725 A | 5/1982 | Cortese et al. | |
| 4,360,019 A | 11/1982 | Portner et al. | |
| 4,487,603 A | 12/1984 | Harris | |
| 4,562,751 A | 1/1986 | Nason et al. | |
| 4,627,850 A | 12/1986 | Deters et al. | |
| 4,628,928 A * | 12/1986 | Lowell | 606/1 |
| 4,678,408 A | 7/1987 | Nason et al. | |
| 4,685,903 A | 8/1987 | Cable et al. | |
| 4,692,147 A | 9/1987 | Duggan | |
| 4,725,852 A | 2/1988 | Gamblin et al. | |
| 4,865,845 A | 9/1989 | Eckenhoff et al. | |
| 5,057,318 A | 10/1991 | Magruder et al. | |
| 5,059,423 A | 10/1991 | Magruder et al. | |
| 5,080,653 A | 1/1992 | Voss et al. | |
| 5,097,122 A | 3/1992 | Colman et al. | |
| 5,112,614 A | 5/1992 | Magruder et al. | |
| 5,137,727 A | 8/1992 | Eckenhoff | |
| 5,193,539 A | 3/1993 | Schulman et al. | |
| 5,193,540 A | 3/1993 | Schulman et al. | |
| 5,234,692 A | 8/1993 | Magruder et al. | |
| 5,234,693 A | 8/1993 | Magruder et al. | |
| 5,292,344 A | 3/1994 | Douglas | |
| 5,312,439 A | 5/1994 | Loeb | |
| 5,501,703 A | 3/1996 | Holsheimer et al. | |
| 5,540,730 A | 7/1996 | Terry, Jr. et al. | |
| 5,690,691 A * | 11/1997 | Chen et al. | 607/40 |
| 5,728,396 A | 3/1998 | Peery et al. | |
| 5,836,994 A * | 11/1998 | Bourgeois | 607/40 |
| 5,938,688 A | 8/1999 | Schiff | |
| 6,016,449 A | 1/2000 | Fischell et al. | |
| 6,051,017 A | 4/2000 | Loeb et al. | |
| 6,091,992 A | 7/2000 | Bourgeois et al. | |
| 6,164,284 A | 12/2000 | Schulman et al. | |
| 6,185,452 B1 | 2/2001 | Schulman et al. | |
| 6,208,894 B1 | 3/2001 | Schulman et al. | |
| 6,219,580 B1 | 4/2001 | Faltys et al. | |
| 6,272,382 B1 | 8/2001 | Faltys et al. | |
| 6,308,101 B1 | 10/2001 | Faltys et al. | |
| 6,327,503 B1 * | 12/2001 | Familoni | 607/40 |
| 6,368,315 B1 | 4/2002 | Gillis et al. | |
| 6,381,496 B1 | 4/2002 | Meadows et al. | |
| 6,487,446 B1 | 11/2002 | Hill et al. | |
| 6,516,227 B1 | 2/2003 | Meadows et al. | |
| 6,539,263 B1 | 3/2003 | Schiff et al. | |
| 6,553,263 B1 | 4/2003 | Meadows et al. | |
| 6,591,137 B1 * | 7/2003 | Fischell et al. | 607/40 |
| 6,609,031 B1 * | 8/2003 | Law et al. | 607/46 |
| 6,620,151 B2 | 9/2003 | Blischak et al. | |
| 6,666,845 B2 | 12/2003 | Hooper et al. | |
| 6,735,474 B1 | 5/2004 | Loeb et al. | |
| 6,740,072 B2 | 5/2004 | Starkweather et al. | |
| 6,760,626 B1 | 7/2004 | Boveja | |
| 6,770,067 B2 | 8/2004 | Lorenzen et al. | |
| 6,941,171 B2 | 9/2005 | Mann et al. | |
| 7,127,297 B2 * | 10/2006 | Law et al. | 607/46 |
| 2002/0072780 A1 | 6/2002 | Foley | |
| 2002/0161414 A1* | 10/2002 | Flesler et al. | 607/40 |
| 2004/0082980 A1 | 4/2004 | Mouine et al. | |
| 2004/0162594 A1* | 8/2004 | King | 607/40 |
| 2004/0172084 A1 | 9/2004 | Knudson et al. | |
| 2004/0193229 A1 | 9/2004 | Starkebaum et al. | |

FOREIGN PATENT DOCUMENTS

| | | |
|---|---|---|
| WO | WO-98/37926 | 9/1998 |
| WO | WO-98/43700 A1 | 10/1998 |
| WO | WO-98/43701 A1 | 10/1998 |
| WO | WO-98/48889 A1 | 11/1998 |
| WO | WO-99/56646 A1 | 11/1999 |
| WO | WO-02/20086 A1 | 3/2002 |
| WO | WO 02/26317 A1 | 4/2002 |
| WO | WO-02/32499 A1 | 4/2002 |
| WO | WO-02/089655 A2 | 11/2002 |

OTHER PUBLICATIONS

Cameron, et al., "Micromodular Implants to Provide Electrical Stimulation of Paralyzed Muscles and Limbs", IEEE Transactions on Biomedical Engineering, vol. 44, No. 9, pp. 781-790 (Sep. 1997).

Cameron, et al.,"Prevalence of Columnar Lined (Barrett's) Esophagus. Comparison of Population Based Clinical and Autopsy Findings", Gastroenterology, vol. 99, (1990), pp. 918 922.

Clouse, et al., "The Esophagus", In Gitnick G, ed. Current Gastroenterology, vol. 14. St. Louis, Mo: Mosby Year Book, Inc., (1994), pp. 1 28.

Demeester, et al., "Gastroesophageal Reflux Disease." In: Moody FG, Carey LC, Jones RS, et al, eds. Surgical Treatment of Digestive Disease. Chicago, Ill: Year Book Medical Publishers, (1989), pp. 65 108.

Eisen, et al.,"The Relationship between Gastroesophageal Reflux Disease and its Complications with Barrett's Esophagus", Am J Gastroenterol, vol. 92, (1997), pp. 27 31.

Fennerty, et al., "The Diagnosis and Treatment of Gastroesophageal Reflux Disease in a Managed Care Environment: Suggested Disease Management Guidelines", Arch Intern Med, vol. 156 (1966), pp. 477 84.

Isolauri, et al., "Natural Course of Gastroesophageal Reflux Disease: 17 22 year follow up of 60 patients." Am J. Gastroenterol, vol. 92 (1997) pp. 37 41.

Johnson, DA., "Medical Therapy for Gastroesophageal Reflux Disease." Am J Med, vol. 92, 5A Suppl. (1992) pp. 88S 97S.

Miros, et al., "Only Patients with Dysplasia Progress t Adenocarcinoma in Barrett's Oseophagus," Gut, vol. 32, (1991), pp. 1441-1446.

Orlando, RC.,"The Pathogenesis of Gastroesophageal Reflux Disease: the Relationship Between Epithelial Defense Dysmotility, and Acid Exposure," Am J Gastroesophageal vol. 92, 4 Suppl., (1997), pp. 3S and 5S.

Peters, et al., "Gastroesophageal Reflux", Surg Clin North Am. vol. 73 (1993), pp. 1119 1144.

Richter, JE., "Surgery for Reflux Disease Reflections of a Gastroenterologist", N Engl J Med., vol. 362, (1992), pp. 825 827 Editorial.

Williamson, et al., "Barrett's Esophagus: Prevalence and Incidence of Adenocarcinoma," Arch Intern Med., vol. 151, (1991), pp. 2212 2216.

Whitehurst, et al. inventors for AB-125U; U.S. Appl. No. 09/929,596, filed Aug. 12, 2001; entitled "Fully Implantable Neurostimulator for Autonomic Nerve Fiber Stimulation as a Therapy for Urinary and Bowel Dysfunction".

* cited by examiner

METHODS FOR TREATING GASTROINTESTINAL DISORDERS

The present invention claims the benefit of U.S. Provisional Patent Application Ser. No. 60/601,801, filed 16 Aug. 2004, which application is incorporated herein by reference in its entirety.

FIELD OF THE INVENTION

The present invention generally relates to implantable stimulator systems and methods, and more particularly relates to implantable stimulator systems and methods utilizing one or more implantable stimulators as a therapy for gastrointestinal disorders, including gastrointestinal motility, sphincteric disorders, and eating disorders.

BACKGROUND OF THE INVENTION

Implantable stimulators are used to treat a variety of patient medical conditions. Such stimulators include a microminiature implantable electrical stimulator, referred to herein as a microstimulator, and known as the BION® microstimulator. The BION microstimulator has been developed (by Advanced Bionics of Valencia, Calif.) to overcome some of the disadvantages of traditional leaded systems. The standard BION device is a leadless microstimulator, as the implantable pulse generator and the electrodes have been combined into a single microminiature package. A standard configuration of the BION device is a cylinder that is about 3 mm in diameter and between about 2 and 3 cm in length. This form factor allows the BION device to be implanted with relative ease and rapidity, e.g., via endoscopic or laparoscopic techniques. With this configuration, the BION device consists of only two electrodes: a reference, or indifferent, electrode at one end and an active electrode at the other end. In addition, with this configuration, electrical signals delivered to nerves travel away from the stimulation location along the nerve fibers in both directions.

The teachings of the present disclosure provide a means of chronically stimulating the nerves and muscles that contribute to the function of the gastrointestinal system with the BION device. Electrical stimulation of such targets may provide significant therapeutic benefit in the management of gastrointestinal motility disorders, sphincteric disorders, and obesity.

Gastrointestinal disorders may be due to a number of underlying etiologies and may manifest a number of symptoms. Gastrointestinal motility disorders, sphincteric disorders, and eating disorders may be caused by musculature that fails to contract, musculature that fails to relax, or musculature that fails to contract and relax in a coordinated fashion. An understanding of these various diseases requires some description of the anatomy and the physiology of the gastrointestinal system.

The gastrointestinal (GI) system consists of the gastrointestinal tract and associated glandular organs that produce secretions. The major structures of the gastrointestinal tract are the mouth, pharynx, esophagus, stomach, small intestine (duodenum, jejunum, and ileum), large intestine (colon), rectum, and anus. Associated glandular organs include the salivary glands, liver, gallbladder, and pancreas.

Most of the GI tract is covered with a thin outermost layer known as the serosa (adventitia), which is primarily connective tissue. Just underneath the serosa is the muscularis externa, which consists of two substantial layers of smooth muscle cells: an inner circular layer and an outer longitudinal layer. Contractions of the muscularis externa mix and circulate the contents of the GI lumen and propel the contents along the GI tract. The layer just below the muscularis externa is the submucosa, which is primarily connective tissue and may also contain secretory glands in some portions. The innermost layer of the GI tract is the mucosa, which is rich in glands, blood vessels, and lymph tissue.

The wall of the GI tract contains many interconnected neurons. The most prominent plexus is the myenteric plexus (Auerbach's plexus), which is located between the outer longitudinal and the inner circular layers of the muscularis externa. The submucosal also contains a major plexus, the submucosal plexus (Meissner's plexus). These two plexuses, along with the other neurons of the GI tract, constitute the enteric nervous system. The enteric nervous system includes both sensory and motor fibers, and many of these are connected to form reflex arcs that can coordinate activity in the absence of extrinsic innervation. Approximately $10^8$ neurons reside in the GI tract, a number comparable to that of the spinal cord.

The sympathetic nervous system also contributes to the innervation of the GI tract, including fibers stemming from the prevertebral and paravertebral ganglia and coursing through the celiac, superior mesenteric, inferior mesenteric, and hypogastric plexuses. Activation of the sympathetic nerves usually inhibits the motor and secretory activities of the GI system. Most of the sympathetic fibers terminate on neurons in the myenteric and submucosal plexuses and not directly on smooth muscle or glands. The sympathetic nervous system also appears to induce contraction of some sphincters.

Parasympathetic innervation of the GI tract arises primarily from the vagus nerve, but the anus, rectum, and distal part of the large intestine receive parasympathetic fibers from the pelvic nerves. The parasympathetic fibers are typically preganglionic, and they synapse with the postganglionic fibers in the wall of the GI tract. These postganglionic fibers directly innervate the smooth muscle and secretory cells of the GI tract.

In GI smooth muscle, the resting membrane potential characteristically varies or oscillates. These baseline oscillations are referred to as slow waves, and the frequency varies from about 3 per minute in the stomach to about 12 per minute in the duodenum. Chemoreceptors and mechanoreceptors, as well as parasympathetic and sympathetic innervation, may modulate these slow waves or may lead to independent and increased activity in response to a food bolus.

One of the primary functions of the GI tract is peristalsis, which is the progressive contraction of successive sections of the inner circular smooth muscle layer of the muscularis externa. These contractions move along the GI tract in order to propel food from the esophagus to the anus. In much of the GI tract, a bolus of food that produces mechanical distention of the GI tract will typically cause contraction of the circular smooth muscle immediately behind the bolus and relaxation of the circular smooth muscle immediately in front of the bolus. The slow waves of the smooth muscle cells tends to determine the timing of peristaltic contractions.

The esophagus is responsible for the transit of food from the pharynx to the stomach. Interestingly, the muscle tissue of the upper one-third of the esophagus is striated, while the muscle tissue of the lower one-third of the esophagus is smooth. Neurons of the myenteric plexus directly innervate the smooth muscle cells of the esophagus and communicate extensively. The esophageal musculature, both striated and smooth, is extrinsically innervated primarily by branches of the vagus nerve. The upper esophageal sphincter (UES) prevents the entry of air into the esophagus. The lower esophageal sphincter (LES) prevents the entry of gastric contents into the esophagus. Normally, when a wave of esophageal peristalsis begins, a reflex causes the LES to relax. Esophageal motility disorders include lack of peristalsis and diffuse esophageal spasm, a medical condition in which the lower part of the esophagus contracts in a prolonged and painful fashion after swallowing. Some individuals suffer from dysfunction of the LES, which may allow gastric juice to move back into the esophagus and erode the esophageal mucosa. This is known as gastroesophageal reflux disease (GERD). Chronic erosion by GERD can lead to a precancerous medical condition known as Barrett's esophagus. Other individuals suffer from achalasia, in which the LES fails to relax sufficiently during swallowing to allow food to enter the stomach.

The major functions of the stomach are to serve as a reservoir following a meal, to break food into smaller particles and begin digestion, and to empty gastric contents into the small intestine at a controlled rate. Normally, when a wave of esophageal peristalsis begins, a reflex causes the upper (proximal) portion of the stomach to relax. When food enters the stomach, gastric contractions begin, which are usually very strong slow wave contractions at the rate of about 3 per minute. These contractions begin near the upper (proximal) portion of the stomach and travel down towards the gastroduodenal junction, also known as the pylorus. As each peristaltic wave reaches the pylorus, the pyloric sphincter snaps shut, so that the stomach empties in small squirts, one for each peristaltic wave. The rapid contractions also serve to break up large food particles and to mix food with digestive juices. If gastric emptying occurs too rapidly, a duodenal ulcer may develop. If the pyloric sphincter allows regurgitation of the duodenal contents, then a gastric ulcer may develop. Some patients suffer from gastroparesis, which is a decrease in or a lack of coordination of gastric contractions.

The small intestine makes up about three-fourths of the length of the GI tract. It is approximately 5 meters in length, and a bolus traverses the small intestine in 2 to 4 hours. The small intestine is the site where most digestion and absorption take place. In addition to peristalsis, the small intestine has a more frequent movement known as segmentation, which is characterized by closely spaced contractions of the inner circular muscle layer of the muscularis externa. These contractions divide the small intestine into small neighboring segments. In rhythmic segmentation, the sites of the circular contractions alternate, so that an individual segment of intestine contracts and then relaxes. Segmentation effectively mixes chyme (digested matter) with secretions and brings material into contact with the mucosal surface for absorption. At the distal end of the small intestine (i.e., the ileum) is the ileocecal sphincter (also known as the ileocecal valve). Normally this sphincter is closed; however, short-range peristalsis in the ileum relaxes the sphincter and allows a small amount of chyme to squirt into the cecum (the first part of the large intestine). Administration of codeine and other opiates decreases small intestinal motility. This increases transit time and allows for more thorough absorption of water, salts, and nutrients, thus markedly reducing the frequency and volume of stools. Patients who have undergone abdominal surgery may experience dysfunction in small or large intestinal motility.

The large intestine (colon) receives about 1 liter of chyme per day. Most of the salts and water entering the colon are absorbed; the feces normally contain only 50-100 ml of water per day. The colon differs from the rest of the GI tract in that the longitudinal muscle of the colon is concentrated in three bands known as the taeniae coli. Additionally, the "peristaltic" wave of the colon is referred to as mass movement. It differs from a normal peristaltic wave in that the contracted segments remain contracted for a significant period of time. Mass movements push the colonic contents a significant length towards the rectum. In Hirschsprung's disease, also known as congenital aganglionic megacolon, enteric neurons are congenitally absent from a part of the colon. Typically only the internal anal sphincter and a short length of adjacent colon are affected. Filling of the rectum by a mass movement leads to reflex relaxation of the distal rectum in a normal person. In patients with Hirschsprung's disease, this reflex relaxation does not occur, and as a result functional obstruction of the distal colon occurs. This leads to dilation of the colon (i.e., megacolon) above the obstruction.

The anal canal is usually kept closed by the internal and external sphincters. The internal anal sphincter is a thickening of the circular smooth muscle of the anal canal. The external anal sphincter is more distal and consists entirely of striated muscle. The external anal sphincter is innervated by somatic motor fibers via the pudendal nerves. This innervation allows the anal sphincter to be controlled both by reflexes and voluntarily. Patients with fecal incontinence are unable to regulate one or both of these sphincters.

In the fasting state, the slow wave activity of the GI tract is significantly attenuated. However, the GI tract continues to have periodic peristaltic contractions to propel food, especially large particles of food, towards the large intestine. These fasting contractions are known as the migrating myoelectric complex (MMC). The MMC begins in the stomach every 75 to 90 minutes in the fasting state, and it travels slowly all the way down to the small intestine.

Some of the GI disorders mentioned above may be treated with medication or with surgery. Some of these, such as fecal incontinence, may not respond well to treatment with either. An overview of three major GI disorders are as follows:

Gastroesophageal Reflux Disease (GERD)

Gastroesophageal reflux disease (GERD), which accounts for 75% of esophageal pathology [DeMeester, et al., "Gastroesophageal Reflux Disease." In: Moody, et al, eds. *Surgical Treatment of Digestive Disease*. Chicago, Ill.: Year Book Medical Publishers; 1989: pages 65-108.], is characterized by a broad spectrum of clinical presentations, from simple heartburn to ulcerative esophagitis, esophageal stricture, and Barrett's metaplasia with its tendency to become malignant.

As many as 10 percent of Americans have episodes of heartburn (pyrosis) every day, and 44 percent have symptoms at least once a month [Orlando R. C., "The Pathogenesis of Gastroesophageal Reflux Disease: the Relationship Between Epithelial Defense, Dysmotility, and Acid Exposure." *Am J Gastroenterol* 1997; 92(4 suppl): pages 3S-5S; and Isolauri, et al., "Natural Course of Gastroesophageal Reflux Disease: 17-22 Year Follow-up of 60 Patients." *Am J Gastroenterol* 1997; 92: pages 3741.]. In all, GERD affects an estimated 25 to 35 percent of the U.S. population [Eisen, et al., "The Relationship Between Gastroesophageal Reflux Disease and Its Complications with Barrett's Esophagus." *Am J Gastroenterol* 1997; 92: pages 27-31.]. Approximately one-third of the patients with heartburn who seek medical care have endoscopic evidence of esophagitis and about 10% to 20% have severe complications of esophagitis [Richter J. E., "Surgery for Reflux Disease—Reflections of a Gastroenterologist", *N Engl J Med.* 1992; 326: pages 825-827. Editorial.].

The major complications of GERD are erosive/ulcerative esophagitis, esophageal stricture, and Barrett's esophagus (a precancerous medical condition), all of which result from the damage inflicted by gastric juice on the esophageal mucosa and changes caused by subsequent repair and fibrosis [Peters, et al., "Gastroesophageal Reflux." *Surg Clin North Am.* 1993; Vol. 73: pages 1119-1144.]. An estimated 10% of patients treated for GERD have peptic stricture. A recent population-based study revealed an autopsy-estimated prevalence of Barrett's esophagus of 376 per 100,000, a greater than 16-fold increase from that of the 22.6 per 100,000 clinically diagnosed cases [Cameron, et al., "Prevalence of Columnar-Lined (Barrett's) Esophagus. Comparison of Population-Based Clinical and Autopsy Findings", *Gastroenterology.* 1990; Vol. 99: pages 918-922.]. Patients with GERD are considered to have a greater incidence of Barrett's esophagus compared to others undergoing endoscopy [Green P H R. "What is the Prevalence of Barrett's in the General Population and in Patients with GERD?" *Syllabus. NY Soc Gastrointest Endosc Postgrad Course.* Nov. 1-11, 1994: pages 2-3.]. The development of Barrett's epithelium remains the most disconcerting complication of reflux disease because of its predisposition to carcinoma [Clouse, et al., "The Esophagus." In: Gitnick G, ed. *Current Gastroenterology. Volume* 14. St. Louis, Mo.: Mosby-Year Book, Inc; 1994: pages 1-28.]. Two recent studies suggest the incidence of adenocarcinoma is one in 96 to 99 patient-years in follow-up [Williamson, et al. "Barrett's Esophagus: Prevalence and Incidence of Adenocarcinoma." *Arch Intern Med.* 1991; Vol. 151: pages 2212-2216; and Miros, et al., "Only Patients with Dysplasia Progress to Adenocarcinoma in Barrett's Oesophagus." *Gut.* 1991; 32: pages 1441-1446.].

Only 5 to 10 percent of patients with erosive esophagitis will fail to heal within 3 months on standard doses of Acid Pump Inhibitor medication (e.g., omeprazole, lansoprazole) [Bardhan K. D., "Is There Any Acid Peptic Disease that is Refractory to Proton Pump Inhibitors?" *Aliment Pharmacol Ther,* 1993; Vol. 7 (suppl 1): pages 13-31.]. However, esophagitis tends to become a relapsing, chronic medical condition. It recurs in 50 to 80 percent of affected patients within six to 12 months after the discontinuation of pharmacologic therapy [Fennerty, et al., "The Diagnosis and Treatment of Gastroesophageal Reflux Disease in a Managed Care Environment: Suggested Disease Management Guidelines." *Arch Intern Med* 1996; Vol. 156: pages 477-84.]. Surgical antireflux procedures provides good to excellent relief of reflux symptoms in 84% to 89% of patients [Peters, 1993]. Such procedures involve reduction of a hiatal hernia, if present, as well as construction of a valve mechanism.

It is estimated that worldwide over $14 billion is spent each year for medications to relieve the symptoms of GERD. As medication only treats the symptoms but not the underlying cause of the disease, most GERD patients need to take daily doses of medication for a lifetime. For a small number of patients, a surgical procedure called fundoplication is available.

Achalasia

Achalasia is a disorder of the esophagus characterized by the reduced ability to move food down the esophagus and the inability of the lower esophageal sphincter to relax in response to swallowing. The disorder is characterized by loss of the wave-like contraction of smooth muscles that forces food through the digestive tract (peristalsis). The medical condition also includes spasms of the valve (sphincter) from the esophagus to the stomach that does not relax and lack of nervous stimulation of the esophagus. Causes include damage to the nerves to the esophagus, parasitic infection, and hereditary factors. Achalasia may occur at any age but increases with frequency with advancing age. The incidence is 2 out of 10,000 people.

The two most common symptoms of achalasia are dysphagia (inability to swallow) and regurgitation of food. Additional symptoms of achalasia may include chest pain that increases after eating, weight loss, drooling, and cough. Complications of achalasia include tearing (perforation) of the esophagus and gastroesophageal reflux disease (GERD).

The approach to treatment is to reduce the pressure at the lower esophageal sphincter (LES). This may be achieved by manipulating the lower esophagus sphincter by special instruments. Medications such as long-acting nitrates or calcium channel blockers may also be used to lower the pressure at the lower esophagus sphincter. Sometimes, botulinum toxin is injected to relax the sphincter. Surgery to decrease the pressure in the lower sphincter (called an esophagomyotomy) may be indicated if other interventions fail. The effectiveness of treatment varies from 60 to 85%, depending on the procedure.

Obesity

Obesity is characterized as an eating disorder causing excessive bodily fat which results from gastrointestinal disorders as described above, and emphasized herein as the inability of the sphincters muscles to contact and open in a normal coordinated fashion. Obesity affects millions of Americans, and a substantial percentage of these people are morbidly obese. These people may also suffer from such obesity-related problems as heart disease, vascular disease, and social isolation. An additional number of Americans may also suffer from various other eating disorders that may result in cachexia (i.e., a general physical wasting and malnutrition) or periods of obesity and/or cachexia. The etiology of obesity is largely unknown. The etiology of some eating disorders is psychological in many patients, but for other patients, is poorly understood.

Patients suffering from morbid obesity and/or other eating disorders have very limited treatment options. For instance, some of these patients may undergo surgery to reduce the effective size of the stomach ("stomach stapling") and to reduce the length of the nutrient-absorbing small intestine. Such highly invasive surgery is associated with both acute and chronic complications, including infection, digestive problems, and deficiency in essential nutrients. In extreme cases, patients may require surgical intervention to a put a feeding tube in place. Patients suffering from eating disorders may suffer long-term complications such as osteoporosis.

As the medical treatments for gastrointestinal motility disorders, sphincteric disorders, and eating disorders have proven ineffective, improvements are still needed for the treatment of these GI disorders providing effective long term results, elimination of the need for lifelong medicine and its attendant side effects, and the relative ease of an endoscopic implantation procedure.

BRIEF SUMMARY OF THE INVENTION

The teachings of the present disclosure address the above and other needs by providing means for chronically stimulating the gastrointestinal nerves and muscles as a therapy for gastrointestinal motility, sphincteric disorders, and obesity.

That is, in one aspect, the present disclosure provides an embodiment of a microstimulator that may be implanted via injection and/or via endoscopic means along the sensory and motor fibers of the enteric nervous system and sympathetic nervous system. A more complicated surgical procedure may be required for sufficient access to a particular nerve (e.g., a nerve surrounded by scar tissue) or for purposes of fixing the microstimulator in place. A single microstimulator may be implanted, or two or more microstimulators may be implanted to achieve greater stimulation of one or more nerves.

In accordance with another aspect of the present disclosure, the microstimulator possess one or more of the following properties, among others:
- at least two leadless electrodes for applying stimulating current to surrounding tissue;
- at least two electrodes located on a surface of a flexible lead, with associated electrical connections embedded in the elongated lead body, wherein electrical stimulation may be directed more locally to targeted tissue(s) a short distance from the surgical fixation site of the microstimulator;
- one or more drugs may be applied to a stimulation site via drug infusion through drug delivery parameters which may cause the drug infusion rate to be intermittent, constant, or bolus;
- electronic and/or mechanical components encapsulated in a hermetic package made from biocompatible material(s);
- an electrical coil or other means of receiving energy and/or information inside the package, which receives power and/or data by inductive or radio-frequency (RF) coupling to a transmitting coil placed outside the body, thus avoiding the need for electrical leads to connect devices to a central implanted or external controller;
- means for receiving and/or transmitting signals via telemetry;
- means for receiving and/or storing electrical power within the microstimulator;
- means for replenishing one or more drugs; and
- a form factor making the microstimulator implantable via a minimal surgical procedure.

In accordance with yet another aspect of the present disclosure, a microstimulator may operate independently, or in a coordinated manner with other implanted devices, or with external devices. For instance, a microstimulator may incorporate means for sensing a patient's medical condition, which it may then use to control stimulation parameters in a closed loop manner. The sensing and stimulating means may be incorporated into a single microstimulator, or a sensing means may communicate sensed information to at least one microstimulator with stimulating means.

In accordance with the teachings of the present disclosure, features provide stimulation that can selectively increase neural and/or muscle activity leading to contraction of one of the GI sphincters, e.g., the lower esophageal sphincter (LES) for the treatment of gastroesophageal reflux disease (GERD), achalasia, and obesity. Relatively low frequency electrical current pulses applied to the muscle of a sphincter, the parasympathetic innervation of a sphincter, or the myenteric plexus of a sphincter are likely to produce such excitation and contraction.

It is a further feature of the present disclosure to provide stimulation that can selectively decrease muscle activity leading to relaxation of one of the GI sphincters, e.g., the LES for the treatment of GERD, achalasia, and obesity. Relatively low frequency electrical current pulses applied to the sympathetic innervation of a sphincter is likely to produce such relaxation.

It is yet another feature of the present disclosure to provide a microstimulator that also includes a means of stimulating GI nerve or muscle either intermittently or continuously. Specific stimulation parameters may provide therapeutic advantages for various forms of motility, sphincteric, or eating disorders.

According to yet another feature of the present disclosure, the stimulation produces rhythmic muscle contraction of a portion of the GI tract via stimulation of the myenteric plexus of that portion or via direct stimulation of the muscle of that portion.

It is an additional feature of the present disclosure to provide an improved method for the treatment of chronic abdominal pain.

BRIEF DESCRIPTION OF THE DRAWINGS

The above and other aspects of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1A:
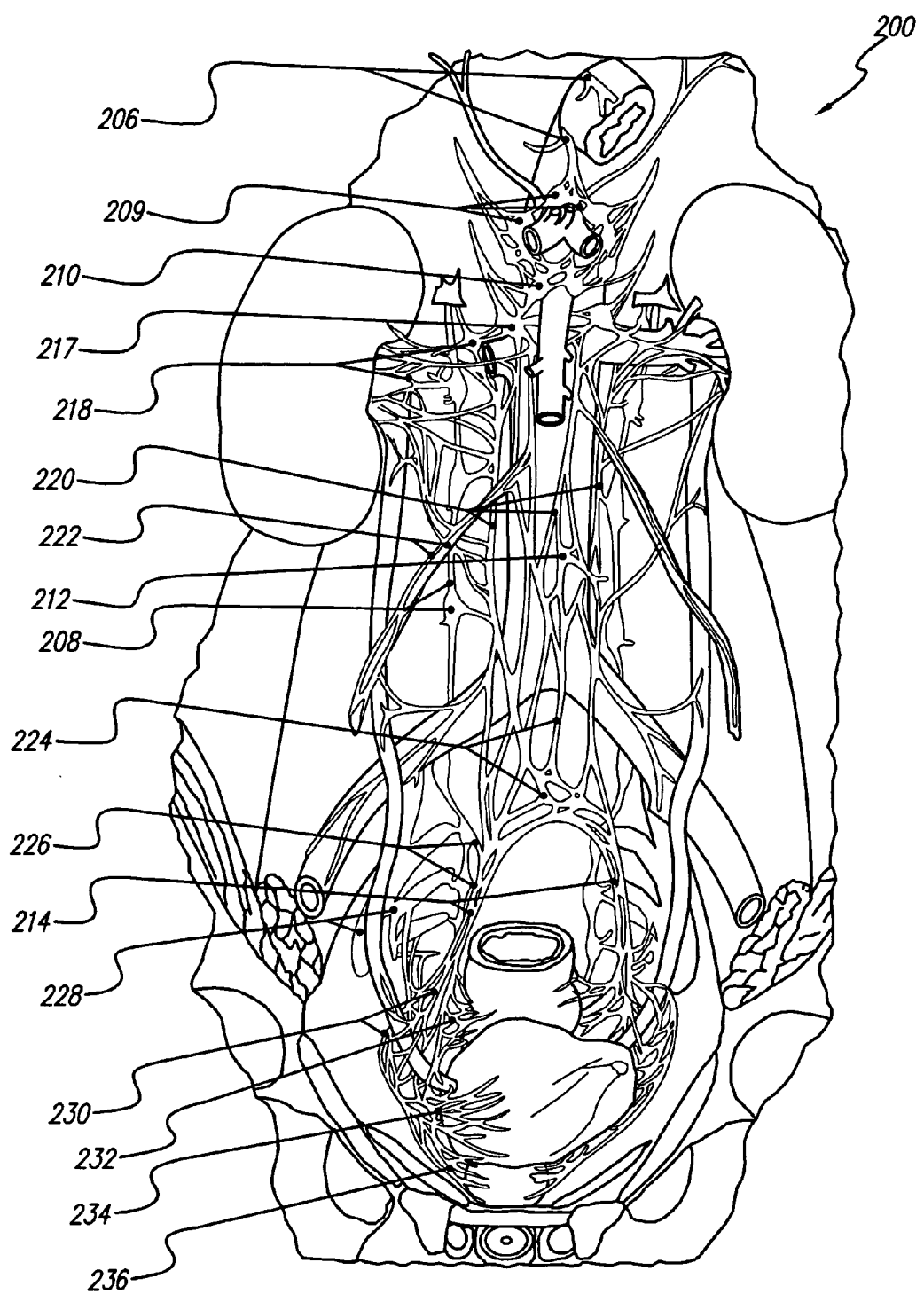
FIG. 1A depicts various nerve branches of the gastrointestinal tract identifying various locations where the microstimulator may be implanted.
Figure 1B:
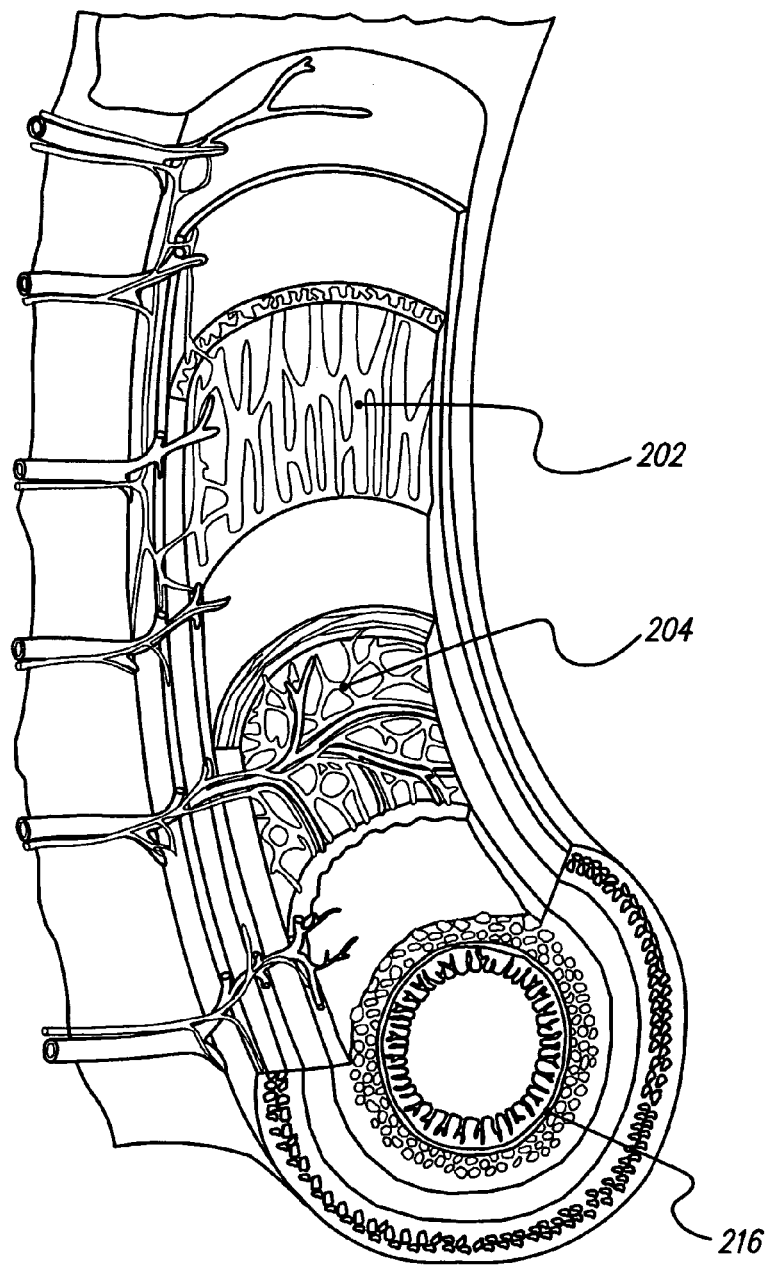
FIG. 1B depicts a sectional view of the intestine showing the location of some of the plexuses where the microstimulator may be implanted.
Figure 2A:
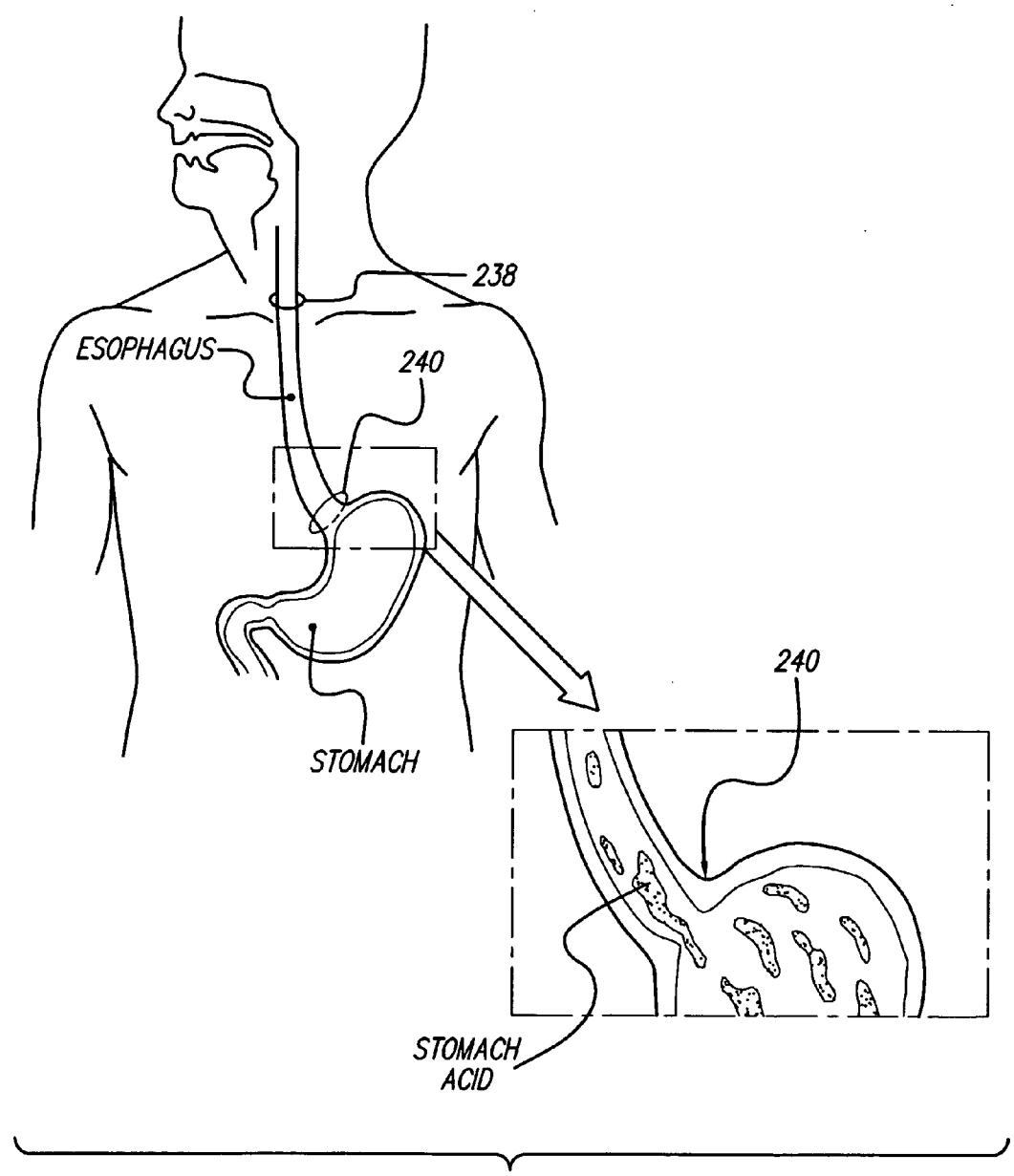
FIG. 2A illustrates some of the major internal structures of the gastrointestinal tract.
Figure 2B:
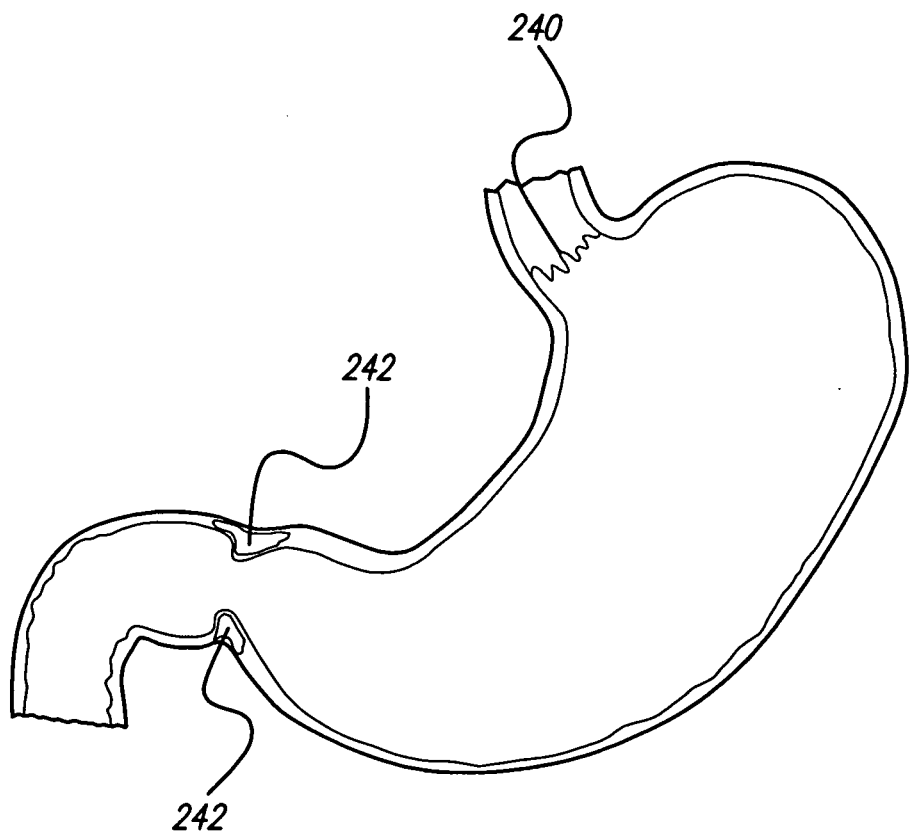
FIG. 2B depicts a view of the stomach where the pylorus and lower esophageal sphincter are located.
Figure 3:
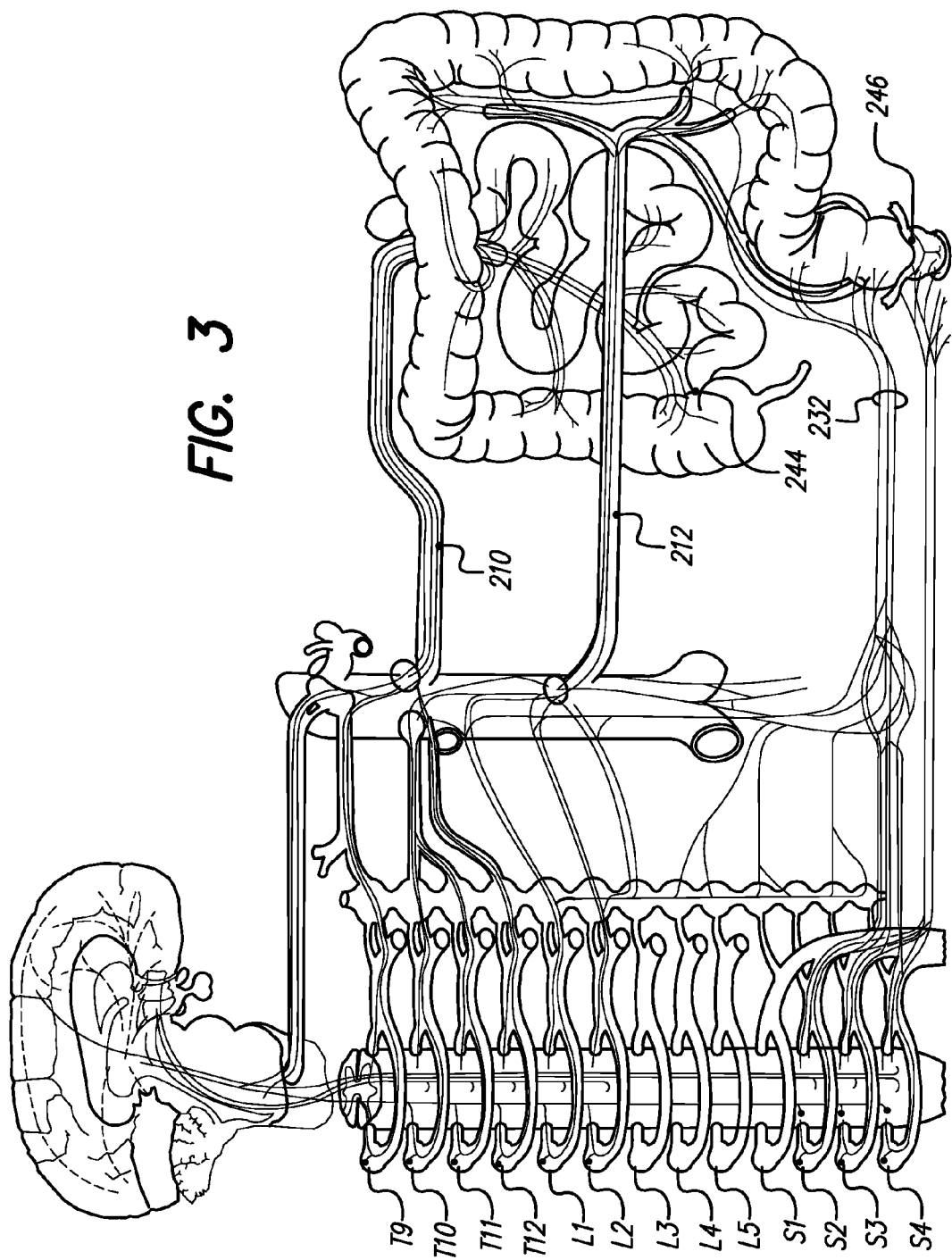
FIG. 3 illustrates the innervation of the small and large intestines.
Figure 4A:
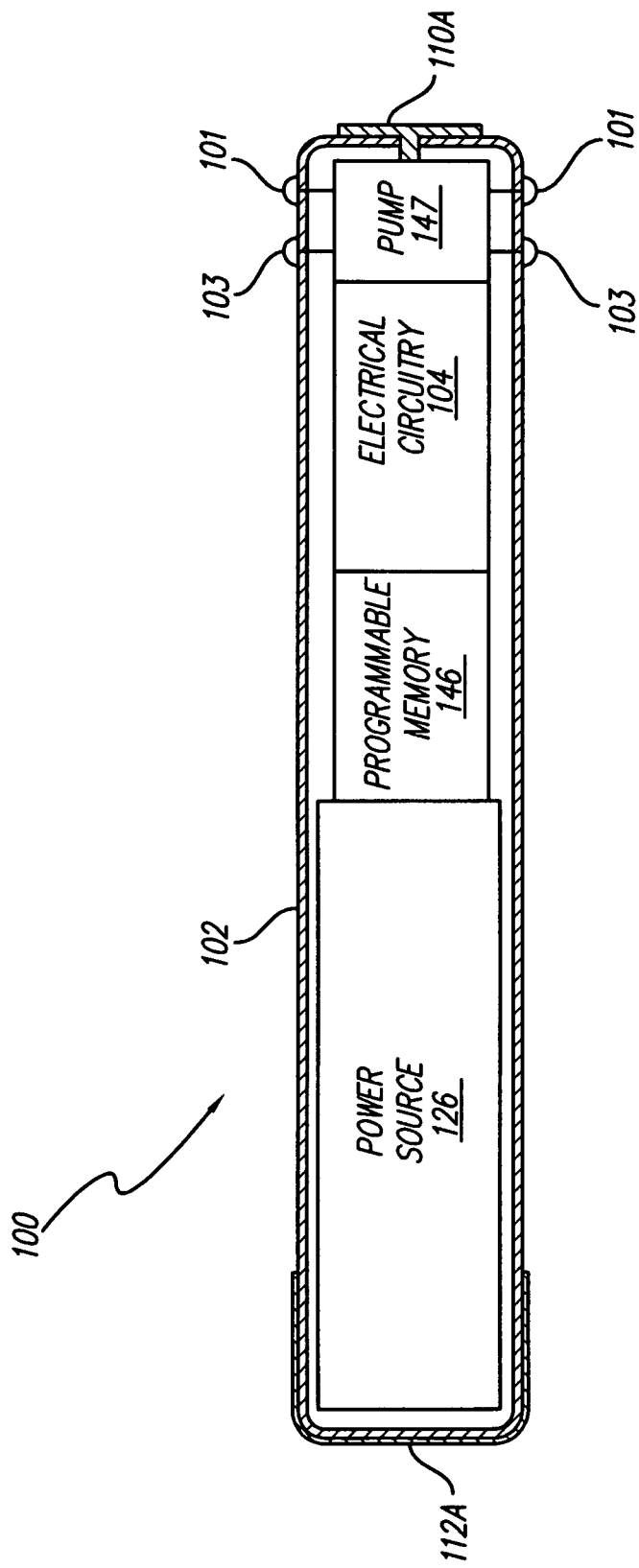
FIG. 4A illustrates an exemplary embodiment of a BION microstimulator that may be used as a stimulation system according to principles described herein.

Turning first to FIGS. 1A and 1B, a miniature implantable microstimulator 100 (e.g., a BION® microstimulator as shown in FIG. 4A) may be implanted via a minimal surgical procedure (e.g., injection via endoscopy such or small laparoscopic incision) adjacent to a portion of the enteric nervous system 200 to treat GI disorders, specifically to treat gastrointestinal motility disorders, sphincteric disorders, and eating disorders by stimulating the areas that include a portion of the myenteric plexus 202, a portion of the submucosal plexus 204, a branch of vagus nerve(s) 206, the sympathetic pelvic plexus 208, one or more of the sympathetic plexuses (i.e., celiac 209, superior mesenteric ganglion 210, inferior mesenteric ganglion 212, and hypogastric plexuses 214), the outer longitudinal layer of the muscularis externa (not shown), and/or the inner circular layer of the muscularis externa 216. Other areas within the enteric nervous system 200 where the implantable microstimulator 100 may be implanted include but are not limited to, the aorticorenal ganglion 217, the renal plexus 218, the intermesenteric plexus 220, the testicular plexus 222, the superior hypogastric plexus 224, the sacral splanchnic nerves 226, the sacral plexus 228, the inferior hypogastric plexus 230, the rectal plexus 232, the vesical plexus 234, the prostatic plexus 236, the upper esophageal sphincter (UES) 238 (shown in FIG. 2A), the lower esophageal sphincter (LES) 240 (shown in FIGS. 2A and 2B), the pyloric sphincter 242 (shown in FIG. 2B), the ileocecal sphincter 244 (shown in FIG. 3), and the internal anal sphincter 246 (shown in FIG. 3). The GI disorders include, but are not limited to, gastrointestinal motility disorders, sphincteric disorders, and eating disorders.

While microstimulator 100 may be implanted via endoscopic and/or laparoscopic means, a more complicated surgical procedure may be required for sufficient access to GI nerve or muscle or for purposes of fixing the microstimulator in place.

The microstimulator 100 includes a programmable memory 146, as shown in FIG. 4A, for storing a set of stimulation and control parameters. This allows stimulation and control parameters to be adjusted to levels that are safe and efficacious with minimal discomfort. Different stimulation parameters may have different effects on neural and/or muscle tissue, and parameters may be chosen to target specific neural and/or muscle populations and to exclude others. For example, relatively low levels of stimulation current are likely to recruit only large diameter fibers. As another example, autonomic fibers tend to demonstrate the greatest response to relatively low-frequency stimulation, i.e., less than 50-100 Hz.

The stimulation can selectively increase neural and/or muscle activity leading to contraction of one of the GI sphincters, e.g., the lower esophageal sphincter 240, for the treatment of gastroesophageal reflux disease (GERD) (disease introduced in the background section of the present disclosure). Relatively low frequency electrical current pulses applied to the muscle of a sphincter, the parasympathetic innervation of a sphincter, or the myenteric plexus of a sphincter are likely to produce such excitation and contraction.

The stimulation can selectively decrease muscle activity leading to relaxation of one of the GI sphincters, e.g., the lower esophageal sphincter 240, for the treatment of achalasia. Relatively low frequency electrical current pulses applied to the sympathetic innervation of a sphincter is likely to produce such relaxation.

The microstimulator 100 also includes a means of stimulating GI nerve or muscle either intermittently or continuously and the application to treat chronic abdominal pain. Specific stimulation parameters may provide therapeutic advantages for various forms of motility, sphincteric, or eating disorders. The stimulation produces rhythmic muscle contraction of a portion of the GI tract via stimulation of the myenteric plexus 202 (shown in FIG. 1B) of that portion or via direct stimulation of the muscle of that portion.

As indicated above, the teachings of the present disclosure are directed to treating gastrointestinal motility, sphincteric disorders, and or obesity using one or more small, implantable microstimulators 100, referred to herein as "microstimulators". The microstimulators 100 of the present disclosure are preferably, but not necessarily, similar to or of the type referred to as BION devices. The following documents describe various features and details associated with the manufacture, operation, and use of BION implantable microstimulators, and are all incorporated herein by reference:

| Application/Patent/ Publication No. | Filing/Publication Date | Title |
|---|---|---|
| U.S. Pat. No. 5,193,539 | Issued Mar. 16, 1993 | Implantable Microstimulator |
| U.S. Pat. No. 5,193,540 | Issued Mar. 16, 1993 | Structure and Method of Manufacture of an Implantable Microstimulator |
| U.S. Pat. No. 5,312,439 | Issued May 17, 1994 | Implantable Device Having an Electrolytic Storage Electrode |
| PCT Publication WO 98/37926 | Published Sep. 3, 1998 | Battery-Powered Patient Implantable Device |
| PCT Publication WO 98/43700 | Published Oct. 8, 1998 | System of Implantable Devices For Monitoring and/or Affecting Body Parameters |
| PCT Publication WO 98/43701 | Published Oct. 8, 1998 | System of Implantable Devices For Monitoring and/or Affecting Body Parameters |
| U.S. Pat. No. 6,051,017 | Issued Apr. 18, 2000 | Improved Implantable Microstimulator and Systems Employing Same |
|  | Published September, 1997 | Micromodular Implants to Provide Electrical Stimulation of Paralyzed Muscles and Limbs, by Cameron, et al., published in IEEE Transactions on Biomedical Engineering, Vol. 44, No. 9, pages 781–790. |

As shown in FIG. 4A, microstimulator device 100 includes a narrow, elongated capsule 102 containing power source 126, programmable memory 146, electronic circuitry 104, pump 147, drug infusion outlets 101, drug replenishing ports 103, and electrodes 110A and 112A. As detailed in the referenced patent publications, electrodes 110A and 112A generally comprise a stimulating electrode (to be placed close to the nerve or muscle) and an indifferent electrode (for completing the circuit). Other configurations of microstimulator device 100 are possible, as is evident from the above-referenced patent publications, and as described in more detail herein.

Figure 4B:
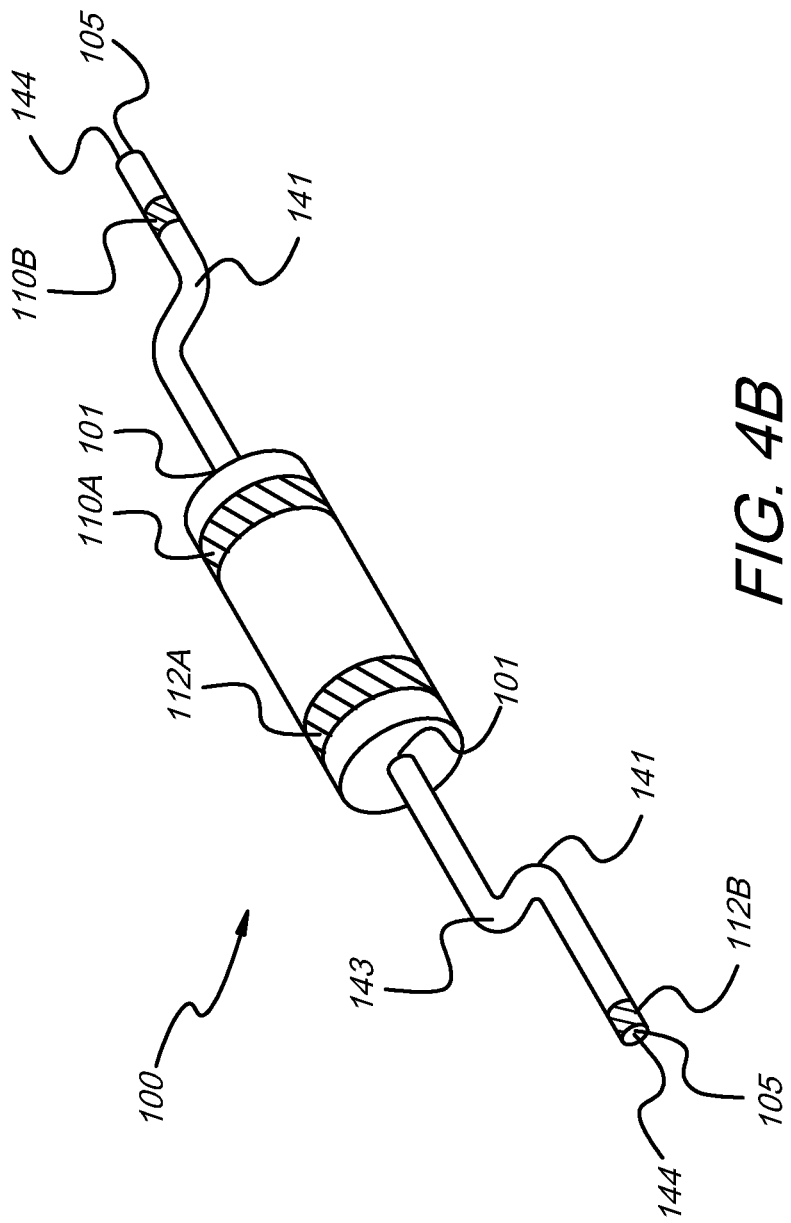
FIG. 4B shows one or more leads coupled to the BION microstimulator according to the principles described herein.

In another embodiment, shown in FIG. 4B, the microstimulator 100 may include two or more leadless electrodes 110A and 112A, as well as electrodes 110B and 112B which may alternatively be located at the distal ends of flexible leads as described in abandoned U.S. patent application Ser. No. 09/624,130 filed Jul. 24, 2000, which is incorporated herein by reference in its entirety. Electrodes 110A and 112A may alternatively be located on a surface of the flexible leads, with associated electrical connections embedded in the elongated body of the lead. The use of such leads permits, among other things, electrical stimulation to be directed more locally to targeted tissue(s) a short distance from the surgical fixation of the bulk of the microstimulator 100, while allowing most elements of the microstimulator 100 to be located in a more surgically convenient site. This minimizes the distance traversed and the surgical planes crossed by the microstimulator 100 and any lead(s).

Certain configurations of implantable microstimulator 100 are sufficiently small to permit its placement adjacent to the structures to be stimulated. (As used herein, "adjacent" and "near" mean as close as reasonably possible to targeted tissue, including touching or even being positioned within the tissue, but in general, may be as far as a distance L1 of about 15 mm to 170 mm, e.g., about 30 mm from the target site.) A single microstimulator 100 may be implanted, or two or more microstimulators 100 may be implanted to achieve greater stimulation of the targeted tissue, or for a longer period of time.

The external surfaces of the microstimulator 100 may advantageously be composed of biocompatible materials. For example, the capsule 102 may be made of glass, ceramic, polymers, metal, or any other material that provides a hermetic package that will exclude water vapor but permit passage of electromagnetic fields used to transmit data and/or power. The electrodes 110A, 112A, 110B, and 112B may be made of a conducting ceramic, conducting polymer, and/or a noble or refractory metal, such as gold, silver, platinum, iridium, tantalum, titanium, titanium nitride, niobium, stainless steel, or their alloys that, e.g., minimize corrosion, electrolysis, and damage the surrounding tissues.

Capsule 102 of FIG. 4A may have a diameter of about 4-5 mm, or only about 3 mm, or even less than about 3 mm. Capsule 102 length may be about 25-35 mm, or only about 20-25 mm, or even less than about 20 mm. The shape of the microstimulator 100 may be determined by the structure of the desired target, the surrounding area, and the method of implantation. A thin, elongated cylinder with electrodes at the ends, as shown in FIG. 4A and FIG. 4B, are possible configurations, but other shapes, such as spheres, disks, or helical structures, are possible, as are additional electrodes.

Microstimulator 100 may be implanted with a surgical insertion tool specially designed for the purpose, or may be injected (e.g., via a hypodermic needle or bore needle). Alternatively, microstimulator 100 may be implanted via conventional surgical methods, or may be inserted using other endoscopic or laparoscopic techniques. A more complicated surgical procedure may be required for fixing the microstimulator in place. As previously mentioned, the microstimulator 100 may be coupled directly to a stimulation site.

Microstimulator 100 contains, when necessary and/or desired, electronic circuitry 104 for receiving data and/or power from outside the body by inductive, radio-frequency (RF), or other electromagnetic coupling. In some embodiments, electronic circuitry 104 includes an inductive coil for receiving and transmitting RF data and/or power, an integrated circuit (IC) chip for decoding and storing stimulation parameters and generating stimulation pulses (either intermittent or continuous), and additional discrete electronic components required to complete the electronic circuit functions, e.g. capacitor(s), resistor(s), coil(s), and the like.

Microstimulator 100 includes, when necessary and/or desired, a programmable memory 146 for storing a set(s) of data, stimulation, and control parameters. Among other things, programmable memory 146 may allow stimulation and control parameters to be adjusted to settings that are safe and efficacious with minimal discomfort for each individual. Specific parameters may provide therapeutic advantages for various forms of gastrointestinal motility disorders and sphincteric disorders. For instance, some patients may respond favorably to intermittent stimulation, while others may require continuous stimulation to alleviate their disorders.

Some embodiments of implantable stimulator 100 also includes a power source and/or power storage device 126. Possible power options for a stimulation device of the present disclosure, described in more detail below, include but are not limited to an external power source coupled to stimulator 100, e.g., via an RF link, a self-contained power source utilizing any suitable means of generation or storage of energy (e.g., a primary battery, a replenishable or rechargeable battery such as a lithium ion battery, an electrolytic capacitor, a super- or ultra-capacitor, or the like), and if the self-contained power source is replenishable or rechargeable, means of replenishing or recharging the power source (e.g., an RF link, an optical link, a thermal link, or other energy-coupling link).

FIG. 4A shows that the microstimulator 100 may also include one or more drug infusion outlets 101 coupled to the pump 147. The infusion outlets 101 facilitate the infusion of one or more drugs into a stimulation site to treat a particular medical condition. The infusion outlets 101 may dispense one or more drugs, chemicals, or other substances directly to the stimulation site. Depending on the patient's symptoms and medical condition, pump 147 may also contain a drug that is dispensed for a limited supply. Once the drug has been depleted, the microstimulator 100 may operate only as a stimulating device. The clinician may also choose to deactivate the microstimulator 100 and replace the microstimulator 100 with a new device having only stimulating capabilities. Microstimulator 100 may also include one or more drug replenishing ports 103 (e.g., for changing or refilling a drug) coupled to the pump 147. Once a drug is depleted, ports 103 may be used to replenish the drug via injection or similar means. Alternatively, as will be described in more detail below, catheters 143 may be coupled to the infusion outlets 101 to deliver the drug therapy to a stimulation site some distance from the body of the microstimulator 100.

FIG. 4B shows an example of a microstimulator 100 with one or more catheters 143 coupled to the infusion outlets 101 on the body of the microstimulator 100. With the catheters 143 in place, the infusion outlets 101 deliver the drug therapy to target tissue located at the ends of catheters 143. Thus, in the example of FIG. 4B, a drug therapy is expelled by the pump 147 shown in FIG. 4A, from an infusion outlet 101 shown in FIG. 4A, through the catheter 143, out an infusion port 144 at the end of the catheter 143, to the stimulation site within the patient. As shown in FIG. 4B, the catheters 143 may also serve as leads 141 having one or more electrodes 110B and 112B disposed thereon. Thus, the catheters 143 and leads 141 of FIG. 4B permit infused drugs and/or electrical stimulation to be directed to a stimulation site while allowing most elements of the microstimulator 100 to be located in a more surgically convenient site. Once a drug has been depleted, catheters 143 may also serve as drug replenishing ports 105 for refilling pump 147. In this instance, the catheters 143 are coupled to replenishing ports 103. The example of FIG. 4B may also include leadless electrodes 110A and 112A disposed on the housing of the microstimulator 100, in the same manner described above for FIG. 4A.

The one or more drugs that may be applied to a stimulation site to treat GI disorders may have an excitatory effect on the stimulation site. Additionally or alternatively, the one or more drugs may have an inhibitory effect on the stimulation site to treat GI disorders. Exemplary excitatory drugs that may be applied to a stimulation site to treat GI disorders include, but are not limited to, at least one or more of the following: an excitatory neurotransmitter (e.g., glutamate, dopamine, norepinephrine, epinephrine, acetylcholine, serotonin); an excitatory neurotransmitter agonist (e.g., glutamate receptor agonist, L-aspartic acid, N-methyl-D-aspartic acid (NMDA), bethanechol, norepinephrine); an inhibitory neurotransmitter antagonist(s) (e.g., bicuculline); an agent that increases the level of an excitatory neurotransmitter (e.g., edrophonium, Mestinon); and/or an agent that decreases the level of an inhibitory neurotransmitter (e.g., bicuculline).

Exemplary inhibitory drugs that may be applied to a stimulation site to treat GI disorders include, but are not limited to, at least one or more of the following: an inhibitory neurotransmitter(s) (e.g., gamma-aminobutyric acid, a.k.a. GABA, dopamine, glycine); an agonist of an inhibitory neurotransmitter (e.g., a GABA receptor agonist such as midazolam or clonidine, muscimol); an excitatory neurotransmitter antagonist(s) (e.g. prazosin, metoprolol, atropine, benztropine); an agent that increases the level of an inhibitory neurotransmitter; an agent that decreases the level of an excitatory neurotransmitter (e.g., acetylcholinesterase, Group II metabotropic glutamate receptor (mGluR) agonists such as DCG-IV); a local anesthetic agent (e.g., lidocaine); and/or an analgesic medication. It will be understood that some of these drugs, such as dopamine, may act as excitatory neurotransmitters in some stimulation sites and circumstances, and as inhibitory neurotransmitters in other stimulation sites and circumstances.

Additional or alternative drugs that may be applied to a stimulation site to treat GI disorders include at least one or more of the following substances: non-steroidal anti-inflammatory medications (NSAIDS) (e.g., ibuprofen, naproxen, VIOXX); estrogens (e.g., estrone, estradiol, estriol, esters of estradiol, synthetic estrogens such as diethylstilbestrol, quinestrol, chlorotrianisene); progestins (e.g., naturally occurring progesterone, medroxyprogesterone acetate, norethindrone acetate, hydroxyprogesterone acetate, norgestrel, norethindrone); antiestrogens (e.g., clomiphene, tamoxifen); gonadotropin releasing hormone agonist analogues (e.g., leuprolide acetate, nafarelin); androgens (e.g., testosterone, testosterone cypionate, fluoxymesterone, fluoxymesterone, danazol, testolactone); antiandrogens (e.g., cyproterone acetate, flutamide); opioids (e.g., morphine); ziconitide; and/or antidepressants (e.g., serotonin specific reuptake inhibitors and tricyclic antidepressants).

Additional substances that may be used to stimulate or modulate activity of the gastrointestinal system, or agonists or antagonists thereof include, but are not limited to, at least one or more of the following: Gastrin, Gastrin Releasing Peptide (GRP), Glucagon-Like Peptide 1 (GLP 1), Glucagon, Neurotensin, Substance P, Neurokinin, Secretin, Somatostatin, Antrin, Prosomatostatin, Pituitary Adenylate Cyclase Activating Peptide (PACAP), Vasoactive Intestinal Peptide (VIP), Ghrelin, Galanin, Galanin-like Peptide, Neuropeptide Y, Peptide YY (PYY), Motilin, Endothelin-1 (ET-1), Endothelin-2 (ET-2), Endothelin-3 (ET-3), Dynorphin A, Endorphin (Beta), Endorphin (Gamma), Enkephalin, Guanylin, Calcitonin Gene Related Peptide (CGRP), Amylin, Pancreatic Polypeptide (PPP), Pancreastatin, Intermedin, and combinations thereof.

Any of the above listed drugs and/or substances, alone or in combination, or other drugs developed or shown to treat GI disorders or its symptoms may be applied to the stimulation site. In some embodiments, the one or more drugs are infused chronically into the stimulation site. Additionally or alternatively, the one or more drugs may be infused acutely into the stimulation site in response to a biological signal or a sensed need (using, e.g., a chemical sensor) for the one or more drugs. Infusion outlets 101 may be used alone or in combination with a catheter to release any of the selected drugs from pump 147. Replenishing ports 103 may be used alone or in combination with a catheter to refill pump 147 with any of the selected drugs and/or substances.

Figure 5:
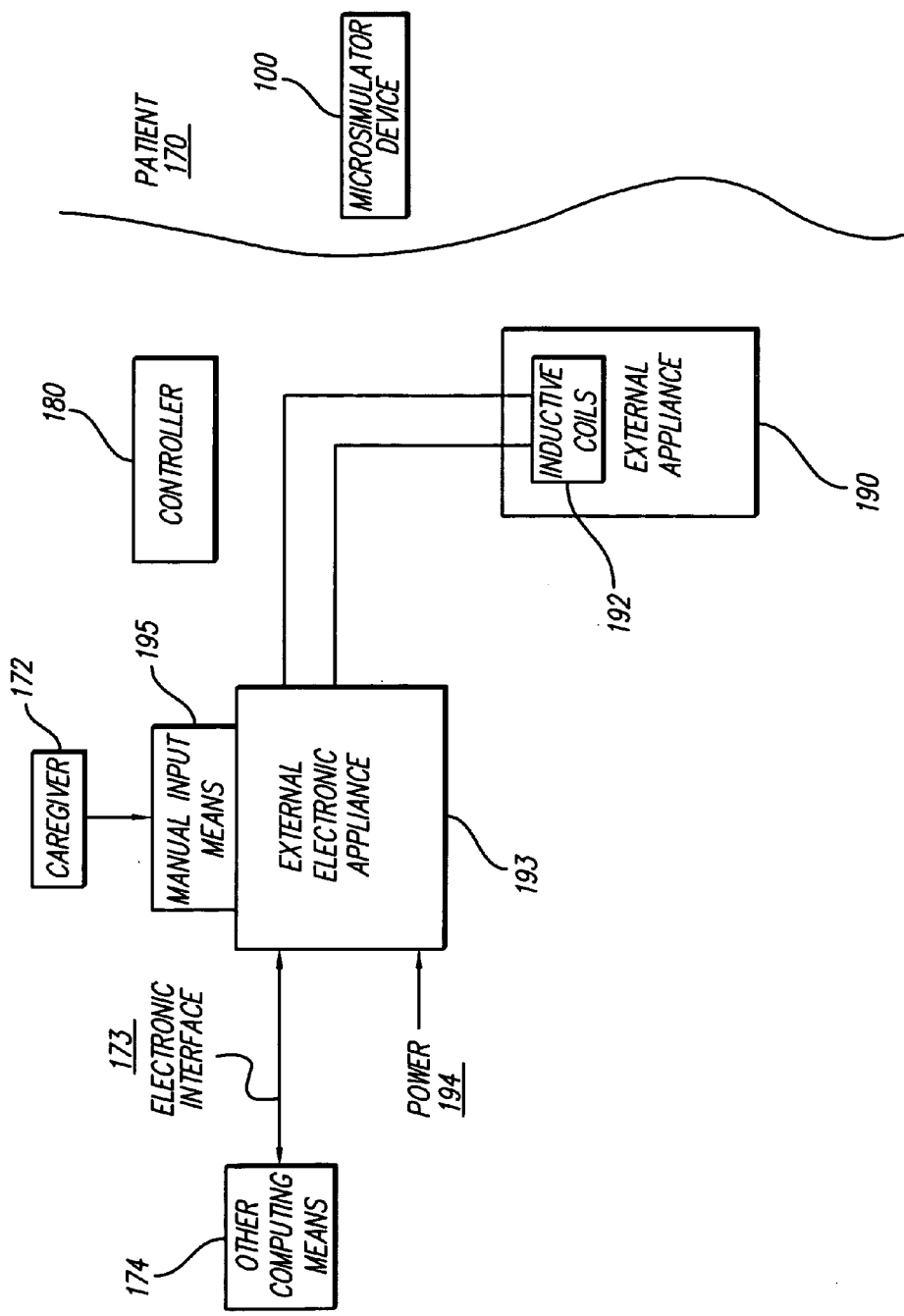
FIG. 5 illustrates exemplary external components used with an exemplary microstimulator device.

Turning next to FIG. 5, which shows exemplary external components used with the microstimulator 100 according to the principles described herein. According to certain embodiments of the present disclosure, a microstimulator 100 operates independently. According to various embodiments of the present disclosure, a microstimulator 100 operates in a coordinated manner with other microstimulator(s), other implanted device(s), or other device(s) external to the patient's body. For instance, a microstimulator 100 may control or operate under the control of another implanted microstimulator(s), other implanted device(s), or other device(s) external to the patient's body. A microstimulator 100 may communicate with other implanted microstimulators, other implanted devices, and/or devices external to a patient's body via, e.g., an RF link, an ultrasonic link, a thermal link, an optical link, or the like. Specifically, a microstimulator 100 may communicate with an external remote control (e.g., patient and/or physician programmer) that is capable of sending commands and/or data to a microstimulator 100 and that may also be capable of receiving commands and/or data from a microstimulator 100.

In certain embodiments, and as illustrated in FIG. 5, the patient 170 switches the implantable stimulator 100 on and off by use of controller 180, which may be handheld. Implantable stimulator 100 is operated by controller 180 by any of various means, including sensing the proximity of a permanent magnet located in controller 180, sensing RF transmissions from controller 180, or the like.

External components for programming and/or providing power to various embodiments of implantable stimulator 100 are also illustrated in FIG. 5. When communication with the implanted stimulator 100 is desired, patient 170 is positioned on or near external appliance 190, which appliance contains one or more inductive coils 192 or other means of communication (e.g., RF transmitter and receiver). External appliance 190 is connected to or is a part of external electronic circuitry appliance 193 which may receive power 194 from a conventional power source. External appliance 193 contains manual input means 195, e.g., a keypad, whereby the patient 170 or a caregiver 172 can request changes in the stimulation parameters produced during the normal operation of the implantable stimulator 100. In these embodiments, manual input means 195 includes various electromechanical switches and/or visual display devices that provide the patient 170 and/or caregiver 172 with information about the status and prior programming of the implantable stimulator 100.

Alternatively or additionally, external electronic appliance 193 is provided with an electronic interface means 173 for interacting with other computing means 174, such as by a serial interface cable or infrared link to a personal computer or to a telephone modem or the like. Such interface means 173 may permit a clinician to monitor the status of the microstimulator 100 and prescribe new stimulation parameters from a remote location.

The external appliance(s) may be embedded in a cushion, pillow, hat, or garment. Other possibilities exist, including a headband, patch or other structure(s) that may be affixed to the patient's body or clothing. External appliances may include a package that may be, e.g., worn on the belt, may include an extension to a transmission coil affixed, e.g., with a VELCRO® band or adhesive, or may be combinations of these or other structures able to perform the functions described herein.

For instance, in several embodiments of the present disclosure, a first and second "stimulator" are provided. The second "stimulator" periodically (e.g. once per minute) records a level of discomfort activity, which it transmits to the first stimulator. The first stimulator uses the sensed information to adjust stimulation parameters according to an algorithm programmed, e.g., by a physician. For example, the amplitude of stimulation may be increased in response to increased activity in nerves or any area of the enteric nervous system 200 (FIG. 1A) which demonstrate increased activity during discomfort or pressure pain in the GI tract. In some alternatives, one stimulator performs both the sensing and stimulating functions.

While a microstimulator 100 may also incorporate means for sensing discomfort (e.g., with a motion or pressure sensor) in the GI tract, it may alternatively or additionally be desirable to use a separate or specialized implantable device to record and telemeter pressure responses in order to adjust stimulation parameters. This information may be transmitted to an external device, such as external appliance 190, or may be transmitted directly to implanted microstimulator(s) 100. However, in some cases, it may not be necessary or desired to include a sensing function or device, in which case stimulation parameters are determined and refined, for instance, by patient feedback, or the like.

Thus, it is seen that in accordance with the teachings of the present disclosure, one or more external appliances may be provided to interact with microstimulator 100, and may be used to accomplish, potentially among other things, one or more of the following functions:

Function 1: If necessary, transmit electrical power from the external electronic appliance 193 via appliance 190 to the implantable microstimulator 100 in order to power the device and/or recharge the power source/storage device 126. External electronic appliance 193 may include an automatic algorithm that adjusts stimulation parameters automatically whenever the implantable microstimulator(s) 100 is/are recharged.

Function 2: Transmit data from the external appliance 193 via the external appliance 190 to the implantable stimulator 100 in order to change the operational parameters (e.g., electrical stimulation parameters) used by microstimulator 100.

Function 3: Transmit sensed data indicating a need for treatment or in response to stimulation from implantable microstimulator 100 to external electronic appliance 193 via external appliance 190.

Function 4: Transmit data indicating state of the implantable stimulator 100 (e.g., battery level, stimulation settings, etc.) to external electronic appliance 193 via external appliance 190.

For the treatment of any of the various types and degrees of discomfort in the GI tract, it may be desirable to modify or adjust the algorithmic functions performed by the implanted and/or external components, as well as the surgical approaches, in ways that would be obvious to skilled practitioners of these arts. For example, in some situations, it may be desirable to employ more than one implantable microstimulator 100, each of which could be separately controlled by means of a digital address. Multiple channels and/or multiple patterns of stimulation might thereby be programmed by the clinician and controlled by the patient.

In some embodiments discussed earlier, microstimulator 100, or a group of two or more microstimulators, is controlled via closed-loop operation. A need for and/or response to stimulation is sensed via microstimulator 100, or by an additional microstimulator (which may or may not be dedicated to the sensing function), or by another implanted or external device. If necessary, the sensed information is transmitted to microstimulator 100. In some embodiments, the stimulation parameters used by microstimulator 100 are automatically adjusted based on the sensed information. Thus, the stimulation parameters are adjusted in a closed-loop manner to provide stimulation tailored to the need for and/or response to stimulation.

Figure 6:
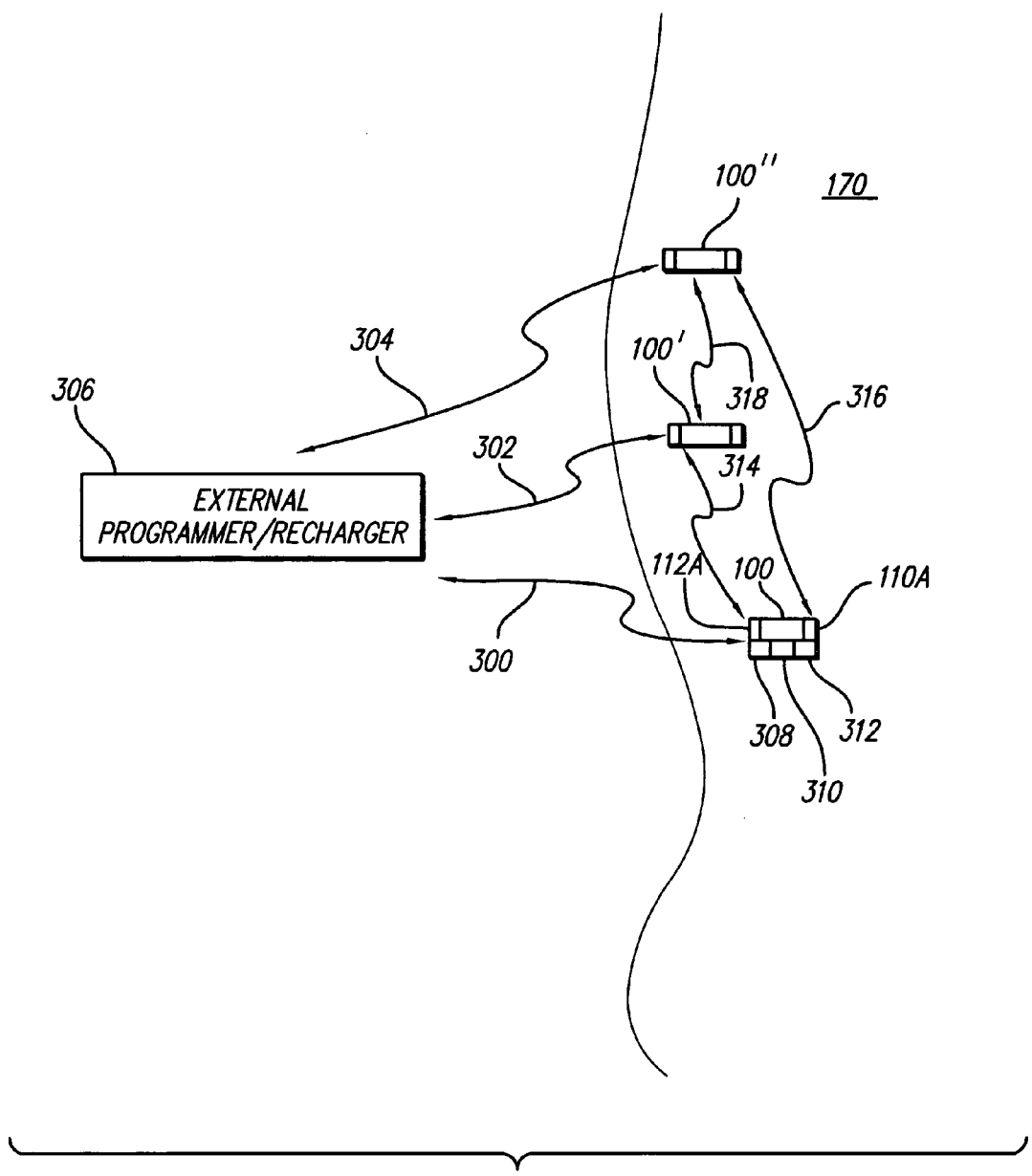
FIG. 6 depicts a system of implantable devices that communicate with each other and/or with external control/programming devices.

For example, as shown in FIG. 6, a first microstimulator 100, implanted beneath the skin of patient 170, provides electrical stimulation via electrodes 110A and 112A to a first location; a second microstimulator 100' provides electrical stimulation to a second location; and a third microstimulator 100" provides electrical stimulation to a third location. As mentioned earlier, the implanted devices may operate independently or may operate in a coordinated manner with other similar implanted devices, other implanted devices, or other devices external to the patient's body, as shown by the control lines 300, 302 and 304 in FIG. 6. That is, in accordance with certain embodiments of the present disclosure, external controller 306 controls the operation of each of the implanted microstimulators 100, 100' and 100".

According to various embodiments of the present disclosure, an implanted device, e.g. microstimulator 100, may control or operate under the control of another implanted device(s), e.g., microstimulator 100' and/or microstimulator 100". That is, a device made in accordance with the teachings of the present disclosure may communicate with other implanted stimulators, other implanted devices, and/or devices external to a patient's body, e.g., via an RF link, an ultrasonic link, a thermal link, an optical link, or other communications link. Specifically, as illustrated in FIG. 6, microstimulator 100, 100', and/or 100", made in accordance with the teachings of the present disclosure, may communicate with an external remote control (e.g., patient and/or physician programmer 306) that is capable of sending commands and/or data to implanted devices and that may also be capable of receiving commands and/or data from implanted devices.

A microstimulator 100 made in accordance with the teachings of the present disclosure may incorporate, in some embodiments, first sensing means 308 (e.g., electrical or chemical sensors) for sensing therapeutic effects, clinical variables, or other indicators of the state of the patient. The microstimulator 100 additionally or alternatively incorporates second means 310 for sensing levels or changes in one or more medications. The microstimulator 100 additionally or alternatively incorporates third means 312 (e.g., electrodes) for sensing electrical current levels and/or waveforms supplied by another source of electrical energy. Sensed information may be used to control the parameters of the microstimulator(s) in a closed loop manner, as shown by control lines 314, 316, and 318. Thus, the sensing means (e.g., electrodes) may be incorporated into a device that also includes electrical stimulation means, or the sensing means (that may or may not have stimulating means) may communicate the sensed information to another device(s) with stimulating means.

While a microstimulator 100 may also incorporate means of sensing (e.g., temperature, chemical, or optical sensors) the medical condition of a patient, it may alternatively or additionally be desirable to use a separate or specialized implantable device to sense and telemeter physiological conditions/responses in order to adjust stimulation parameters. This information may be transmitted to an external device, such as external appliance 193, or may be transmitted directly to implanted microstimulator(s) 100. However, in some cases, it may not be necessary or desired to include a sensing function or device, in which case stimulation parameters may be determined and refined, for instance, by patient feedback.

A microstimulator 100 may incorporate means of sensing indicators of feeding or fasting, e.g., via a pressure sensor on a portion of the GI tract sensing a bolus of food. Sensed information may be used to control the stimulation parameters of a microstimulator or microstimulators in a closed loop manner. According to one embodiment of the present disclosure, the sensing and stimulating means are both incorporated into a single microstimulator 100. According to another embodiment of the present disclosure, the sensing means are incorporated into at least one microstimulator 100 (that may or may not have stimulating means), and the sensing information is communicated to at least one other microstimulator 100 with stimulating means (e.g. electrodes). The sensing means may include, e.g., chemical, pressure, motion, optical, or electrical sensors.

In summary, a conservative estimate of the total US population with esophagitis is 1 percent, or about 3 million Americans. At least 5% of these may be refractory to medication, and a significantly greater percentage will experience a relapse within a year of discontinuing medication. Thus, at least 150,000 patients will consider surgery, and up to ten times more will be dependent on lifelong medication. A number of these patients might consider the microstimulator 100 as a treatment for GERD due to the relative ease of an endoscopic implantation procedure and the elimination of the need for lifelong medicine and its attendant side effects. Patients with GERD (especially those with esophagitis, strictures, and Barrett's metaplasia) may be significantly aided by a microstimulator 100 placed in the lower esophageal sphincter (LES) 240 that allows them to open and close the LES 240 at will, i.e., to open it when eating and to close it otherwise. The microstimulator 100 may also be implanted in other areas of the enteric nervous system 200 shown in FIG. 1A.

Furthermore, patients with achalasia may be significantly aided by the microstimulator 100 placed in the LES 240 that allows them to open and close the LES 240 at will, i.e., to open it when eating and to close it otherwise. Patients would benefit even more from a series of microstimulator(s) 100 that would mimic normal peristalsis; the restoration of peristaltic activity might induce a reflex opening of the LES 240, which would resolve the problem of LES spasm.

In some embodiments of the present disclosure, patients with obesity and/or the like may be significantly aided by a microstimulator 100 placed in the lower esophageal sphincter (LES) 240 that allows them to open and close the LES 240 at will, i.e., to open it when eating and to close it otherwise. Benefits include the promotion of normal metabolism, weight control, and prevention of diabetes and other medical conditions caused or worsened by obesity and/or eating disorders. The microstimulator 100 may also be implanted in other areas of the enteric nervous system 200 shown in FIG. 1A.

Additional potential uses of the present disclosure include, but are not limited to, treatment of chronic abdominal pain, which may be a potential result from the stimulation treatment of the above medical conditions.

The stimulation treatment of the GI tract described herein has been specific to the use of a leadless microstimulator shown in FIG. 4A and a leaded microstimulator shown in FIG. 4B having the above described functions relating to, but not limited to, the use of two or more electrodes, drug infusion parameters, drug replenishing parameters, transmission of stimulating signals, transmission of receiving signals, storing programming signals, and the hermetic packaging for the electronic and mechanical components within an implantable device. It will be recognized that the implantable device may also include a stimulator, a spinal cord stimulator (SCS), a cochlear implant, a deep brain stimulator, a drug pump, a microstimulator, a micro-drug pump or any other type of implantable stimulator. The implantable device described herein may include an implantable pulse generator (IPG) coupled to a lead of electrodes configured to deliver electrical and/or drug stimulation.

Exemplary IPGs suitable for use as described herein include, but are not necessarily limited to, those disclosed in U.S. Pat. Nos. 6,381,496, 6,553,263; and 6,760,626. All of these listed patents are incorporated herein by reference in their respective entireties.

Exemplary spinal cord stimulators suitable for use as described herein include, but are not necessarily limited to, those disclosed in U.S. Pat. Nos. 5,501,703; 6,487,446; and 6,516,227. All of these listed patents are incorporated herein by reference in their respective entireties.

Exemplary cochlear implants suitable for use as described herein include, but are not necessarily limited to, those disclosed in U.S. Pat. Nos. 6,219,580; 6,272,382; and 6,308,101. All of these listed patents and are incorporated herein by reference in their respective entireties.

Exemplary deep brain stimulators suitable for use as described herein include, but are not necessarily limited to, those disclosed in U.S. Pat. Nos. 5,938,688; 6,016,449; and 6,539,263. All of these listed patents are incorporated herein by reference in their respective entireties.

Exemplary drug pumps suitable for use as described herein include, but are not necessarily limited to, those disclosed in U.S. Pat. Nos. 4,562,751; 4,678,408; 4,685,903; 5,080,653; 5,097,122; 6,740,072; and 6,770,067. Additional drug pumps may include convective drug delivery system, e.g., systems based upon electroosmosis, vapor pressure pumps, electrolytic pumps, effervescent pumps, piezoelectric pumps and osmotic pumps. Such pumps or controlled drug release devices suitable for use as described herein include, but are not necessarily limited to, those disclosed in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,360,019; 4,487,603; 4,627,850; 4,692,147; 4,725,852; 4,865,845; 5,057,318; 5,059,423; 5,112,614; 5,137,727; 5,234,692; 5,234,693; 5,728,396; 6,368,315 and the like. All of these listed patents are incorporated herein by reference in their respective entireties.

Exemplary microstimulators suitable for use as described herein include, but are not necessarily limited to, those disclosed in U.S. Pat. Nos. 5,193,539; 5,193,540; 5,312,439; 6,185,452; 6,164,284; 6,208,894; and 6,051,017. All of these listed patents are incorporated herein by reference in their respective entireties.

Exemplary micro-drug pumps suitable for use as described herein include, but are not necessarily limited to, those disclosed in U.S. Patent Pub. No. 2004/0082908 and U.S. Pat. Nos. 5,234,692; 5,234,693; 5,728,396; 6,368,315; 6,666,845; and 6,620,151. All of these listed patents and publication are incorporated herein by reference in their respective entireties.

Exemplary gastrointestinal tract stimulation treatments are described in the following United States Patents, U.S. Publications, and PCT Publications: U.S. Pat. Nos. 6,091,992; 5,540,730; 5,292,344; 5,690,691; 2002/0072780; 2004/0172084; 2004/0193229; WO 09/956,646; WO 09/848,889; WO 09/731,679; WO 02/032499; and WO 02/020086, which patents and publications are incorporated herein by reference in their respective entireties.

While the invention herein disclosed has been described by means of specific embodiments and applications thereof, numerous modifications and variations could be made thereto by those skilled in the art without departing from the scope of the invention set forth in the claims.

What is claimed is:

1. A method for treating a patient suffering from obesity, comprising:
    providing at least one stimulator coupled to at least two electrodes implanted within the patient;
    using at least one external appliance to transmit stimulation parameters;
    generating stimulation pulses with the at least one stimulator in accordance with the stimulation parameters; and
    delivering the stimulation pulses via the at least two electrodes to a lower esophageal sphincter of the patient, wherein the at least one stimulator is operated, such that the lower esophageal sphincter is opened when the patient is eating and closed when the patient is not eating.

2. The method of claim 1 further comprising:
    providing at least one sensor;
    using the at least one sensor to sense physiological information; and
    determining the stimulation parameters based upon the sensed physiological information.

3. The method of claim 2 wherein the at least one sensor is a part of the stimulator.

4. The method of claim 1 further comprising:
    providing a pump having at least one infusion outlet; and
    delivering with the pump via the at least one infusion outlet a drug to the lower esophageal sphincter;
    wherein the pump is part of the stimulator.

5. The method of claim 4 further comprising:
    providing at least one catheter in communication with the pump; and
    delivering the drug to the lower esophageal sphincter via the at least one catheter.

6. The method of claim 1 wherein at least one of the electrodes is located on a surface of at least one flexible lead.

7. The method of claim 1, further comprising implanting the at least one stimulator within the patient.

8. A method for treating a patient suffering from obesity, comprising:
    providing at least one stimulator coupled to at least two electrodes implanted within the patient;
    providing at least one sensor;
    using the sensor to sense physiological information;
    configuring one or more stimulation parameters to treat the obesity in accordance with the sensed physiological information;
    generating stimulation pulses in accordance with the stimulation parameters; and
    delivering the stimulation pulses via the at least two electrodes to a lower esophageal sphincter of the patient, wherein the at least one stimulator is operated, such that the lower esophageal sphincter is opened when the patient is eating and closed when the patient is not eating.

9. The method of claim 8 wherein the at least one sensor is a part of the stimulator.

10. The method of claim 8 wherein at least one of the electrodes is located on a surface of at least one flexible lead.

11. The method of claim 8 further comprising:
    providing a pump having at least one infusion outlet; and
    delivering with the pump via the at least one infusion outlet a drug to the lower esophageal sphincter;
    wherein the pump is part of the stimulator.

12. The method of claim 11 further comprising providing at least one additional infusion port at the end of at least one flexible catheter, wherein the catheter is part of the stimulator.

13. The method of claim 8, further comprising implanting the at least one stimulator within the patient.

14. A method of treating a patient suffering from obesity, comprising:
    providing a stimulator;
    configuring one or more stimulation parameters to treat the obesity;
    programming the stimulator with the one or more stimulation parameters;
    generating an electrical stimulation current configured to treat the obesity with the stimulator in accordance with the one or more stimulation parameters; and
    applying the electrical stimulation current with the stimulator to a lower esophageal sphincter of the patient, wherein the at least one stimulator is operated, such that the lower esophageal sphincter is opened when the patient is eating and closed when the patient is not eating.

15. The method of claim 14 further comprising:
    providing at least one sensor;
    using the at least one sensor to sense physiological information; and
    determining the stimulation parameters based upon the sensed physiological information.

16. The method of claim 15 wherein the at least one sensor is a part of the stimulator.

17. The method of claim 14 further comprising:
    providing a pump having at least one infusion outlet; and
    delivering with the pump via the at least one infusion outlet a drug to the lower esophageal sphincter;
    wherein the pump is part of the stimulator.

18. The method of claim 17 further comprising:
    providing at least one catheter in communication with the pump; and
    delivering the drug to the lower esophageal sphincter via the at least one catheter.

19. The method of claim 17 further comprising:
    providing at least one replenishing port coupled to the pump; and
    using the at least one replenishing port to refill the pump with the drug.

20. The method of claim 19 further comprising providing at least one additional replenishing port at the end of at least one flexible catheter, wherein the catheter is part of the stimulator.

21. The method of claim 14 wherein at least one of the electrodes is located on a surface of at least one flexible lead.

* * * * *